United States Patent
Kyogashima et al.

(10) Patent No.: US 6,537,977 B1
(45) Date of Patent: *Mar. 25, 2003

(54) ANTI-INFLAMMATORY AGENT

(75) Inventors: Mamoru Kyogashima, Higashiyamato (JP); Akira Asari, Iruma (JP)

(73) Assignee: Seikagaku Corporation, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/043,124
(22) PCT Filed: Sep. 19, 1996
(86) PCT No.: PCT/JP96/02706
  § 371 (c)(1),
  (2), (4) Date: May 12, 1998
(87) PCT Pub. No.: WO97/11096
  PCT Pub. Date: Mar. 27, 1997

(30) Foreign Application Priority Data

Sep. 19, 1995 (JP) ............................................. 7-266409

(51) Int. Cl.⁷ ........................ A61K 31/726; A01N 25/00
(52) U.S. Cl. ........................... 514/54; 514/56; 514/886
(58) Field of Search ............................. 514/54, 56, 886

(56) References Cited

U.S. PATENT DOCUMENTS 5,310,881 A * 5/1994 Sakurai et al. .............. 530/395
5,540,931 A * 7/1996 Hewitt et al. ................ 424/434
5,612,321 A * 3/1997 Nguyen ......................... 514/54

FOREIGN PATENT DOCUMENTS

| EP | 0 346 810 | 12/1989 |
| EP | 0 671 414 | 9/1995 |
| JP | 2-40327 | 9/2000 |
| WO | WO 93/05075 | 3/1993 |
| WO | WO 93/050756 | 3/1993 |

OTHER PUBLICATIONS

Bazzoni et al, Journal of Laboratory and Clinical Medicine (1993), 121(2), 268–75.*

Yaakov Naparstek, et al., Arthritis and Rheumatism, vol. 33, No. 10, pp. 1554 to 1559, "Binding of Anti–DNA Antibodies and Inhibition of Glomerulonephritis in MRL–lpr/lpr Mice by Heparin", Oct. 1990.

Kinzo Nagasawa, et al., Carbohydrate Research, vol. 131, pp. 301 to 314, "The Structure of Rooster–Comb Dermatan Sulfate Characterization and Quantitative Determination of Copolymeric, Isomeric Tetra– and Hexa–Saccharides", 1984.

* cited by examiner

Primary Examiner—James O. Wilson
Assistant Examiner—Everett White
(74) Attorney, Agent, or Firm—Oblon, Spivak, McClelland, Maier & Neustadt, P.C.

(57) ABSTRACT

A pharmaceutical composition, which contains glycosaminoglycan having at least one sulfate group or a pharmaceutically acceptable salt thereof, and an immunosuppressant.

10 Claims, 10 Drawing Sheets

Administration time (minute)

FIG. 4A
FIG. 4B
4a: Normal kidney tissue
4b: Kidney tissue with MC(microchange)
4c: Diffuse proliferative lupus nephritis
Magnification x 500    Bar=10 $\mu$ m
FIG. 4C 6a: Normal control  6c:Intermidiate angiitis 6b:Histology slight  6d: Serious angiitis

ANTI-INFLAMMATORY AGENT

BACKGROUND OF THE INVENTION

1. Field of the Invention

The present invention relates to an anti-inflammatory agent, especially to an anti-inflammatory agent against inflammation such as protracted inflammation (chronic progressive inflammation) or inflammation in which immunological mechanism participates.

More specifically, the present invention relates to a potentiator of immunosuppressant potentiating anti-inflammatory effect thereof or an agent enhancing anti-inflammatory effect.

According to the present invention, the onset and/or progress of diseases, such as glomerulonephritis, collagen diseases or related diseases thereof, intractable angiitis, immunological anomalies accompanied with inflammation or autoimmune diseases etc. can be prevented or treated.

2. Description of the Background

Inflammation in which immunological mechanism participates, for example, glomerulonephritis, collagen diseases or related diseases, intractable angiitis, immunological anomalies accompanied with inflammation or autoimmune diseases etc. chronically progresses by repeating acute exacerbation and, without treatment, causes organ deterioration, resulting in renal failure or other organ failures and eventually death. Most of such a chronic progressive inflammation are intractable the causes of the onset thereof have been thought to be immunological anomalies and continuous activation of inflammatory mediator accompanied therewith. Various kinds of therapy have been investigated focusing on these causes. For example, with respect to immunological anomalies, an immunosuppressant such as adrenocorticosteroid, cyclophosphamide, mizoribine, methotrexate or azathioprine is used in a usual manner or in salvage intravenous infusion therapy (pulse therapy). However, adrenocorticosteroid shows serious adverse effects such as suppressive action on adrenal function, easy infectiousness, peptic ulcer, hypertension, osteoporosis and so on. In addition, other immunosuppressants also show extremely serious adverse effects such as bone marrow suppression, onset of gastrointestinal disorders, liver damages, interstitial pneumonia, renal disorders or hemorrhagic urocystitis and so on. In addition, since this kind of pharmacotherapy is not an etiotropic therapy and is carried out by administrating an agent for long duration to cause serious adverse effects, it will cause extremely serious problems. Further, some of those diseases are drug-resistant. Against diseases whose main lesions are nephritis or angiitis, an anti-platelet agent or an anti-coagulant can be used. However, whenever an anti-coagulant such as heparin or warfarin (trade name;general name, Warfarin potassium) is used, hemorrhage has to be cared as an adverse effect. As for an anti-platelet agent, risk of hemorrhage has to be considered. Because among collagen diseases, there are many patients with decreased level of platelet such as in the case of systemic lupus erythematosus (SLE) or many patients with pulmonary hemorrhage such as in the case of Good pasture syndrome accompanied with glomerulonephritis it is difficult to use an anti-platelet agent in such a case as above. Further, though it was reported recently that heparin or low molecular weight heparin was effective for preventing nephritis accompanied with SLE (Japanese unexamined patent application 40327/1990, Arthritis Rheum. 33, 1554, 1990), the effect was not so sure according to the experimental result by the present inventors as described later.

SUMMARY OF THE INVENTION

It is an object of the present invention to provide a pharmaceutical composition containing glycosaminoglycan having at least one sulfate group or a pharmaceutically acceptable salt thereof, and an immunosuppressant.

DETAILED DESCRIPTION OF THE PREFERRED EMBODIMENTS

Inflammation in which immunological mechanism participates, such as, glomerulonephritis, collagen diseases or related diseases thereof, intractable angiitis, immunological anomalies accompanied with inflammation, or autoimmune diseases comprises SLE described above. By considering the above situation and investigating an action of dermatan sulfate or pharmaceutically acceptable salt thereof on these inflammatory diseases using MRL (Ipr/lpr) mice (lzui S., et al., Mechanism of genetic control of murine systemic lupus erythematosus. In systemic Lupus Erythematosus, pp. 3–12, Ed. Peter A. Miescher, Springer-Verlag Berlin, 1995) as an animal model of SLE, the present inventors found that the compound not only suppressed inflammation and delayed the progress of disease, but also had an excellent safety and can be used for a long duration. Further, the effect of dermatan sulfate was investigated using animal model of human multiple sclerosis, rat with experimental allergic encephalomyelitis as another example of inflammation in which immunological mechanism participates, and found to be effective for these diseases. A certain type of dermatan sulfate with specific physical properties or with specific origin, or pharmacologically acceptable salt thereof among various types of dermatan sulfate was found to keep serum level thereof for longer duration and be preferable. That is, dermatan sulfate or pharmaceutically acceptable salt thereof suitable for practice of the present invention was found to be one comprising 2–9%, preferably 3–8%, of Di-OS ($\Delta$HexA1$\rightarrow$3GalNAc); with 0.8–2.0 of intrinsic viscosity (100 mL/g); with 25,000–100,000, preferably 30,000–60,000, of molecular weight which was determined by gel permeation method using high performance liquid chromatography and glycosaminoglycan whose molecular weight was known as a standard (see reference example 1, (1)Determination of molecular weight which was described in Biochim. Biophys. Acta, 1117, 60–70, 1992); or dermatan sulfate derived from crest. The present invention was accomplished by these observations.

An object of the present invention is to provide an anti-inflammatory agent having an excellent anti-inflammatory effect on inflammation using an action of dermatan sulfate or pharmaceutically acceptable salt, especially effective for prevention or treatment of intractable inflammation such as glomerulonephritis, which is inflammation related with immunological mechanism or protracted inflammation, collagen diseases or related diseases thereof intractable angiitis, immunological anomalies accompanied with inflammation, or autoimmune diseases. Another object of the present invention is to provide an agent enhancing anti-inflammatory effect of immunosuppressant in combination with glycosaminoglycan having sulfate group.

The present invention relates to an anti-inflammatory agent comprising dermatan sulfate or pharmaceutically acceptable salt thereof as an effective ingredient as described above. Specifically, the present invention relates to an anti-inflammatory agent comprising dermatan sulfate as an effective ingredient which exhibit an anti-inflammatory effect on protracted inflammation or inflammation with immunological mechanism such as inflammation accompanied with autoimmune diseases. The present invention, more specifically, relates to an anti-inflammatory agent useful for inflammation accompanied with multiple sclerosis, collagen diseases or related diseases thereof, glomerulonephritis, intractable angiitis and the like. In addition, the present invention relates to an anti-inflammatory agent comprising dermatan sulfate with specific physical properties or with specific origin or pharmaceutically acceptable salt thereof. Further, the present invention relates to an enhancing agent which enhances anti-inflammatory effect of an immunosuppressant and comprises glycosaminoglycan having sulfate group or pharmaceutically acceptable salt thereof as an effective ingredient. Further, the present invention relates to an agent enhancing anti-inflammatory effect of an immunosuppressant which comprises glycosaminoglycan having sulfate group or pharmaceutically acceptable salt thereof and an immunosuppresing compound (immunosuppressant).

As glycosaminoglycan having sulfate group which is used in combination with an immunosuppressant, dermatan sulfate, heparin, heparan sulfate, chondroitin sulfate and keratan sulfate are exemplified. Among them, dermatan sulfate is preferable and dermatan sulfate with specific physical properties or with specific origin as described above or pharmaceutically acceptable salt thereof is more preferable.

"a" represents the analytical results of BUN and b represents the analytical results of creatinine. And * in b represents significant difference with $p<0.05$ by Bonferroni examination.

FIG. 4 exhibits histological microphotograph showing the results of autopsy of kidney of mice administered with dermatan sulfate (magnification:×500, –(bar) is 10 $\mu$m).

"a" represents normal kidney tissue, b represents kidney tissue with MC minimal change) and c represents kindly tissue with DP corresponding to proliferative glomerulonephritis among diffuse glomerulonephritis defined by WHO and falling into dysfunction).

FIG. 5 exhibits the rate of abnormal glomeruli when dermatan sulfate was administered in mice in example 2.

"a" represents the rate of the number of MC (minimal change) glomeruli to the total number of glomeruli and b represents the rate of the number of DP glomeruli to the total number of glomeruli.

FIG. 6 exhibits histological microphotographs showing renal artery when dermatan sulfate was administered in mice in example 2 (magnification:×204, –(bar) is 50 $\mu$m).

"a" represents histology of normal control, and b, c and d represents histology of slight, intermediate and serious angiitis, respectively.

Figure 7:
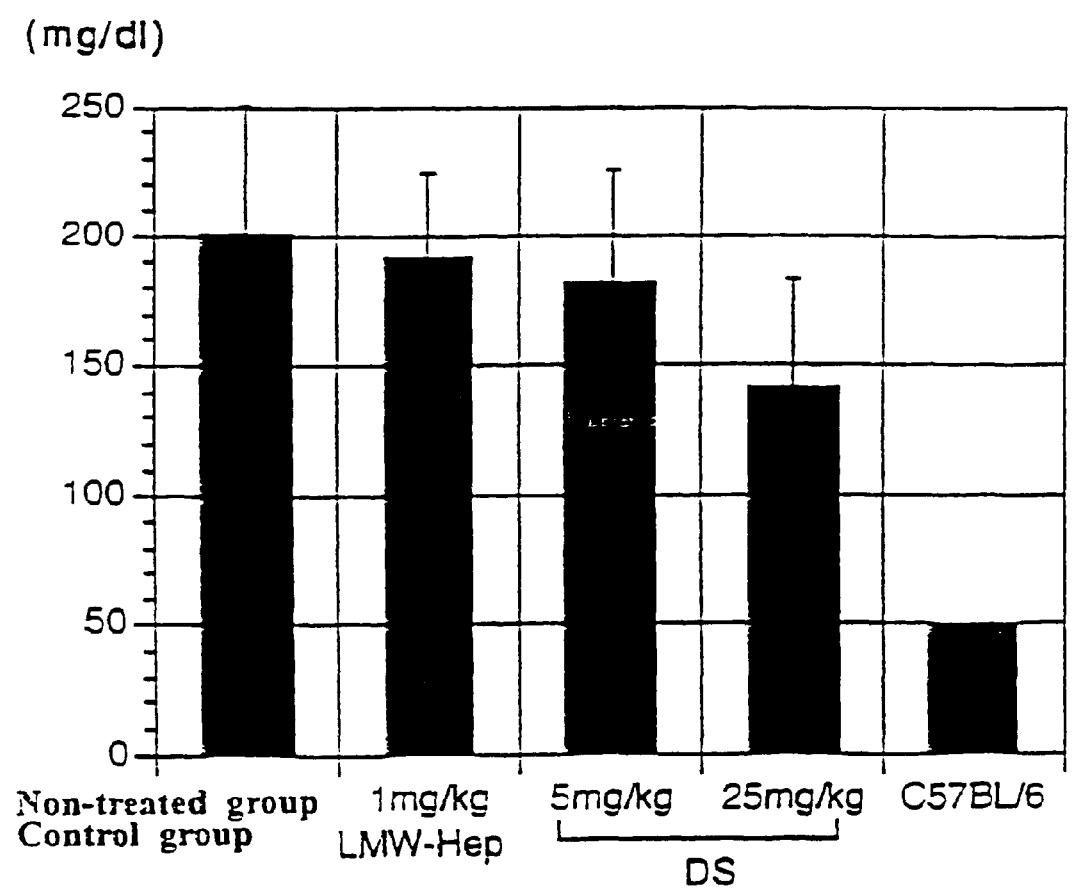

FIG. 7 exhibits the analytical results of fibrinogen in blood when dermatan sulfate was administered in mice in example 2.

Figure 8:
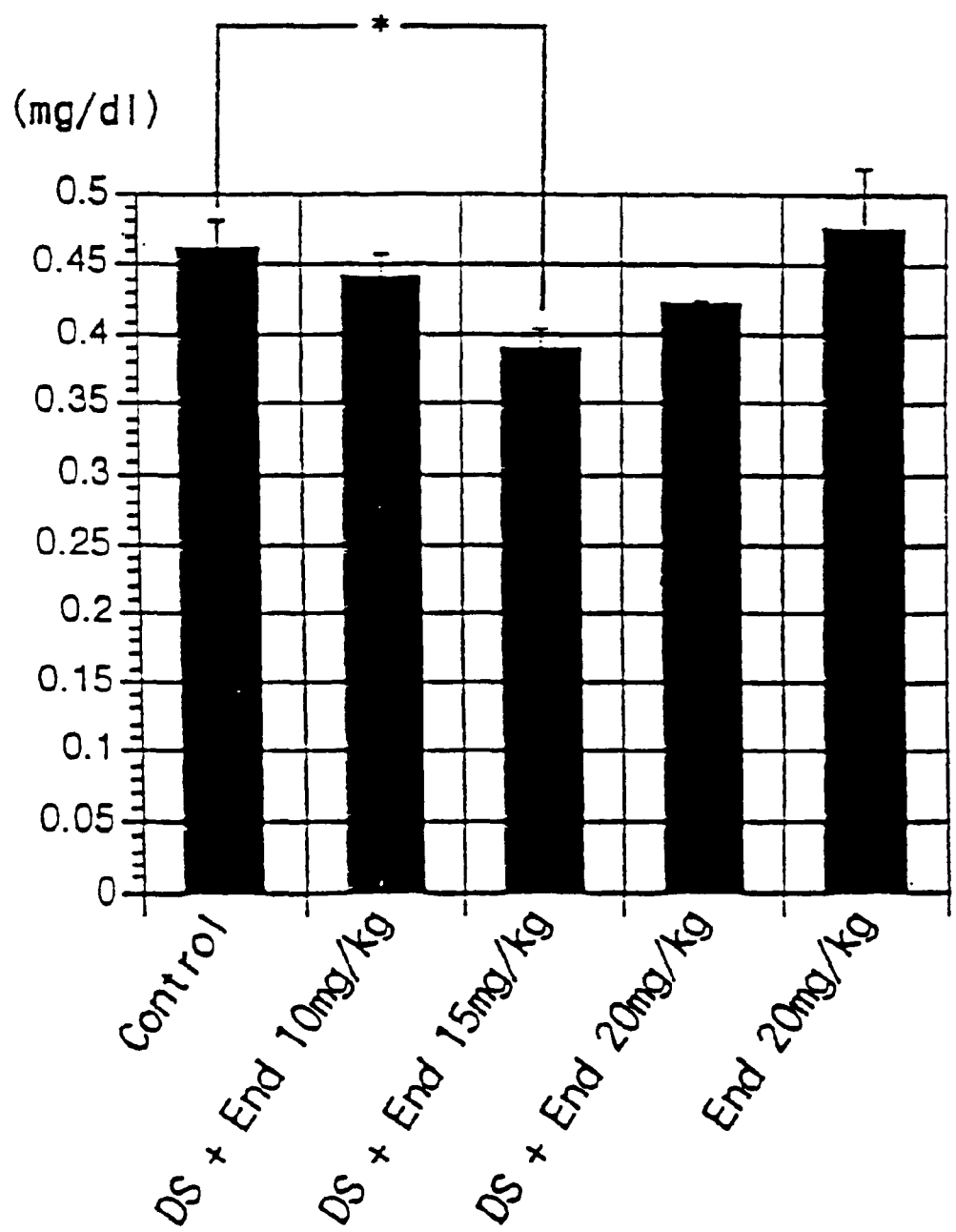

FIG. 8 exhibits the effects of dermatan sulfate (25 mg/kg) and each dosage of endoxane (trade name of cyclophosphamide) by single administration or combined administration on serum level of creatinine in mice in example 3.

DS means dermatan sulfate and End means endoxane. * means significant difference with $p<0.05$ by Bonferroni examination.

Figure 9:
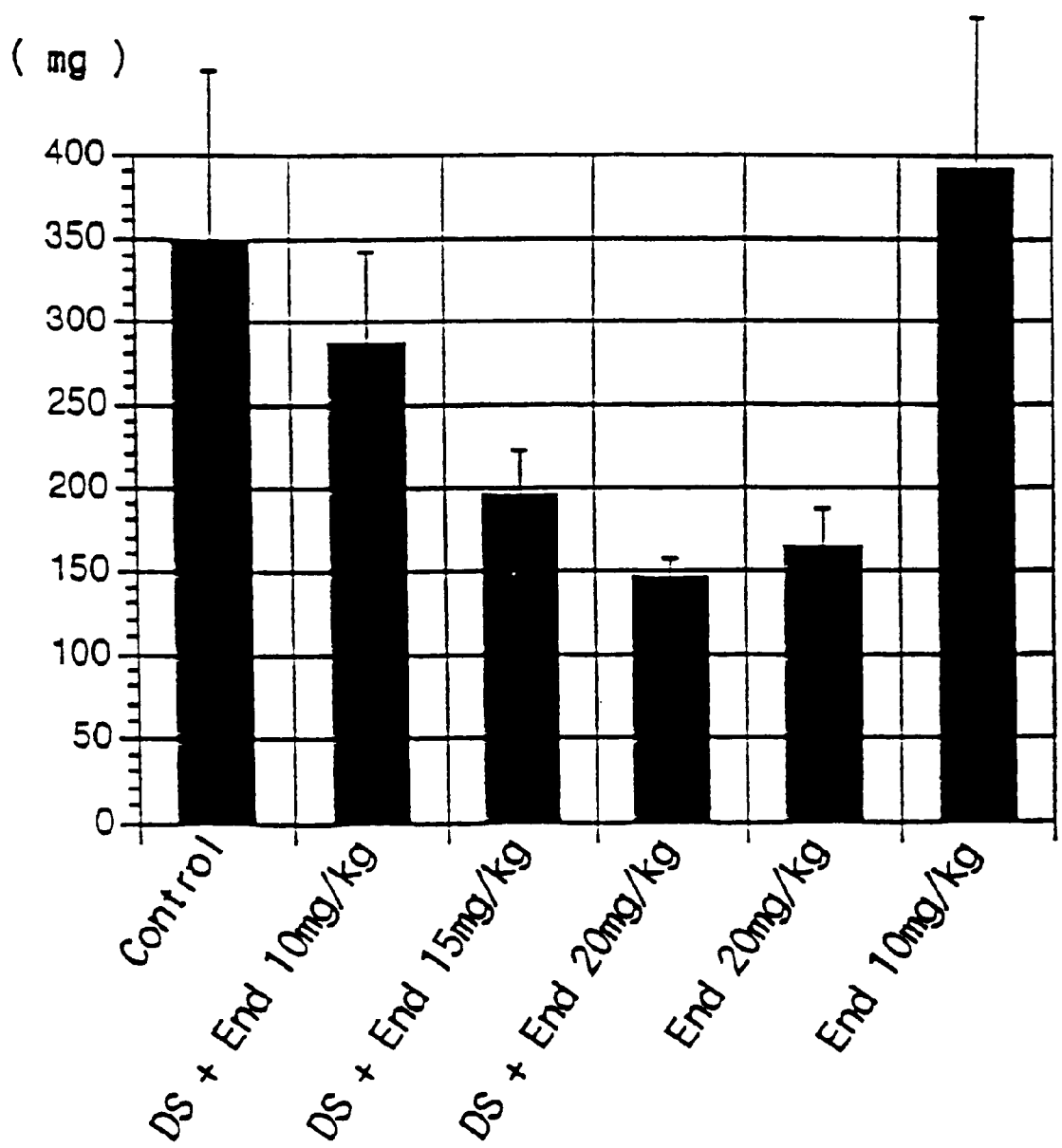

FIG. 9 exhibits the effects of dermatan sulfate (25 mg/kg) and each dosage of endoxane by single administration or combined administration on the weight of spleen in mice in example 3.

DS means dermatan sulfate and End means endoxane.

Figure 10:
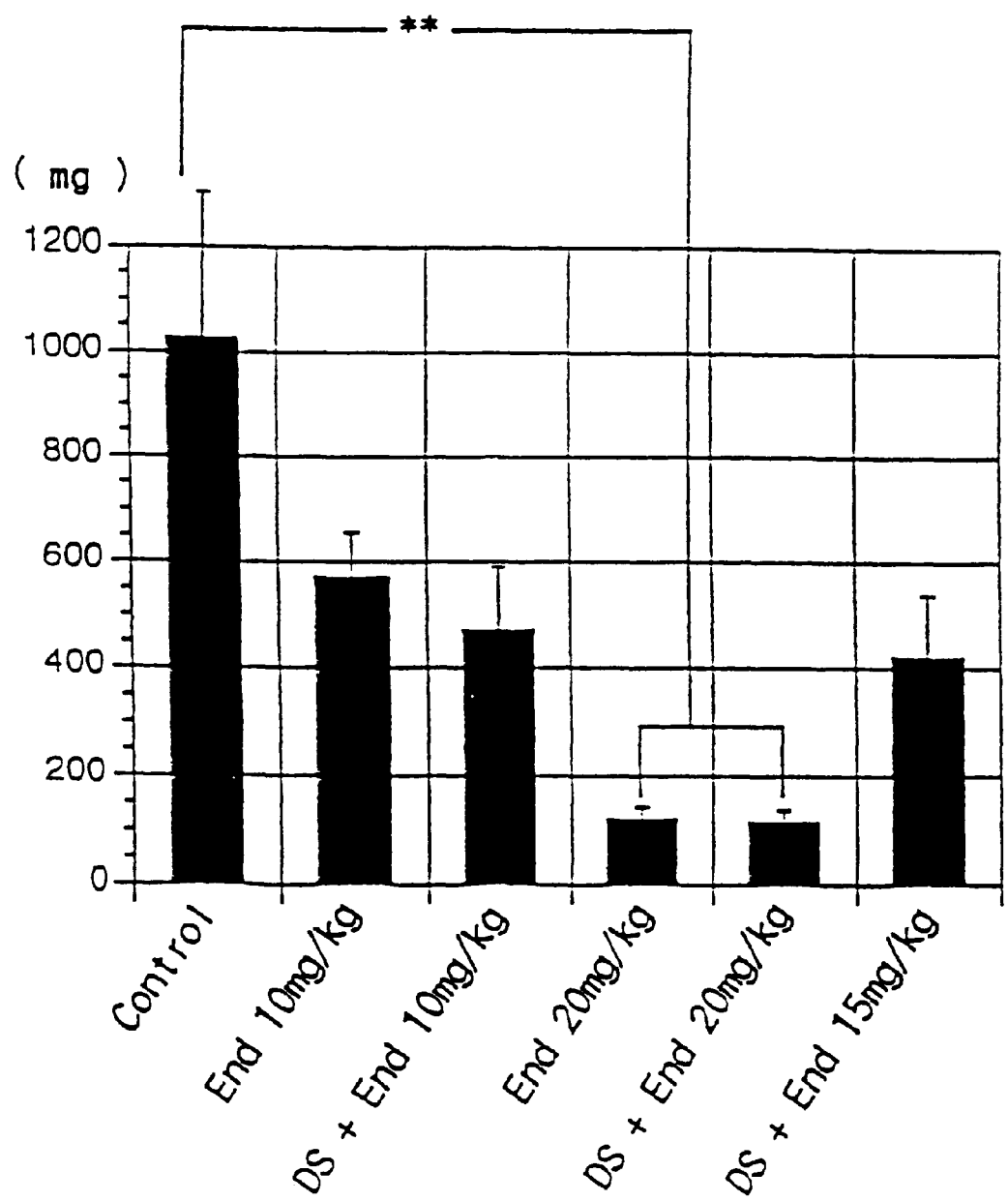

FIG. 10 exhibits the effects of dermatan sulfate (25 mg/kg) and each dosage of endoxane by single administration or combined administration on the weight of mesenteric lymph node in mice in example 3.

** means significant difference with $p<0.01$ by Bonferroni examination.

BEST MODE FOR PRACTICE OF THE INVENTION

Dermatan sulfate comprises, mainly, repeated structure (Ido-GalNAc) of disaccharide consisting of N-acetyl-D-galactosamine-4-sulfate and L-iduronic acid and a small amount of D-glucuronic acid. The content of sulfate, linked position of sulfate group and the content of D-glucuronic acid of dermatan sulfate are different from each other depending on animal species, tissue or organ.

Usually, dermatan sulfate is prepared from raw material such as intestinal mucosae, skin, lung, kidney, liver, pancreas, artery, spleen, brain, thymus, cartilage or crest of mammal such as cattle, pig, horse, sheep, goat, rabbit and so on, or birds such as chicken, duck, goose and so on.

As dermatan sulfate or pharmaceutically acceptable salt thereof used in the present invention(hereinafter, "dermatan sulfate" means including pharmaceutically acceptable salt thereof except on noting something specifically), any compound which is already known in this field can be used and physical properties and origin thereof are not limited.

Compounds derived from, for example, organs (intestine, skin, kidney, blood vessel) of animal(mammal and birds etc.), more specifically, crest, bovine intestine, porcine intestine, porcine skin, bovine kidney, porcine kidney, bovine aorta and with the physical properties, for example, showed in table 1 (average molecular weight, intrinsic viscosity, disaccharide composition) are exemplified.

Dermatan sulfate with relatively low molecular weight of 1,600–10,000 is known (see Dol, F. et al., J. Lab. Clin. Med., 1990, vol. 115, 43–51 or Bianchini, P. et al., Thrombosis and Haemostasis, 1991, vol. 65, 1315 or Barbanti, M. et al., Thrombosis and Haemostasis, 1993, vol. 69, 147–151) and can be used in the present invention. The disaccharide composition in the present invention is the composition(%) of unsaturated disaccharide obtained by the method known in the art, wherein dermatan sulfate is degraded with chondroitinase ABC into unsaturated disaccharide and fractionated the degraded products through high performance liquid chromatography using ion exchange carrier (see "2·8 Structure analysis by glycosaminoglycan degrading enzyme in association with HPLC" in Shin-seikagaku-jikken-koza 3, Tou-situ II, p49–62 (1991) Tokyo-kagaku-doujin, specifically see reference example 1). Unsaturated disaccharide is usually represented by signals demonstrated in table 1 and the structure of isomer represented by each signal is demonstrated by the following formula [I] and table 2.

TABLE 1 various kinds of dermatan sulfate

| Origin | bovine intestine | porcine intestine | porcine skin | crest |
|---|---|---|---|---|
| Average Molecular weight (dalton) | 16,000 | 18,500 | 14,000 | 38,000 |
| Intrinsic viscosity (100 ml/g) | 0.68 | 0.58 | 0.44 | 1.21 |
| Disaccharide composition (%) | | | | |
| ΔDi-0S | 0.69 | 0.69 | 0.34 | 4.97 |
| ΔDi-6S | 2.52 | 4.85 | 0.85 | 4.41 |
| ΔDi-4S | 87.22 | 83.83 | 90.22 | 82.91 |
| ΔDi-diS$_D$ | 0.16 | 0.51 | 0.22 | 0.92 |
| ΔDi-diS$_B$ | 7.65 | 6.31 | 8.38 | 6.13 |
| ΔDi-diS$_E$ | 1.58 | 3.59 | 0.00 | 0.65 |
| ΔDi-triS | 0.18 | 0.24 | 0.00 | 0.00 |

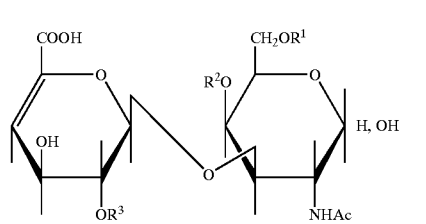

[I]

($R^1$, $R^2$ and $R^3$ in the formula represent hydrogen or $SO_3$—, and Ac represents acetyl group)

TABLE 2

| Code | $R^1$ | $R^2$ | $R^3$ |
|---|---|---|---|
| ΔDi-0S | H | H | H |
| ΔDi-6S | $SO_3$— | H | H |
| ΔDi-4S | H | $SO_3$— | H |
| ΔDi-diS$_D$ | $SO_3$— | H | $SO_3$— |
| ΔDi-diS$_E$ | $SO_3$— | $SO_3$— | H |
| ΔDi-dis$_B$ | H | $SO_3$— | $SO_3$— |
| ΔDi-triS | $SO_3$— | $SO_3$— | $SO_3$— |

The structure demonstrated by abbreviated code in table 1 and 2 is sometimes represents as follows:
ΔDi-OS: ΔHexA1→3GalNAc, ΔDi-6S: ΔHexA1→3GalNAc(6S), ΔDi-4S: ΔHexA1→3GalNAc(4S), ΔDi-diS$_D$: ΔHexA(2S) 1→3GalNAc(6S), ΔDi-diS$_E$: ΔHexA1→3GalNAc(4, 6-diS), ΔDi-diS$_B$: ΔHexA(2S) 1→3GalNAc(4S), ΔDi-triS: ΔHexA(2S)1→3GalNAc(4, 6-diS)

In the above formula, ΔHexA represents unsaturated hexuronic acid and GalNAc represents N-acetyl-D-galactosamine, and ( ) demonstrates the linked position and the number of bonds.

Any of dermatan sulfate described above can be used in the present invention, but dermatan sulfate with the following physical properties and origin characterized by long life span in blood and few adverse effect such as hemorrhage etc. can be preferably used:

(1) The content of ΔDi-OS (ΔHexA1→3GalNAc) is 2–9%, preferably 3-8%; (2)with 0.8–2.0 of intrinsic viscosity (100 ml/g); (3) with 25,000–100,000, preferably 30,000–60,000, of average molecular weight which was determined by gel permeation method using high performance liquid chromatography and gly-cosaminoglycan whose molecular weight was known as a standard (the method described in Biochim. Biophys. Acta, 1117, 60–70, 1992); (4) or dermatan sulfate derived from crest. Dermatan sulfate having the above four features or equivalent thereof is more preferable. As such dermatan sulfate, sodium salt of dermatan sulfate (see Table 1) prepared from crest according to the method described in the specification of patent application(see PCT international publication, WO95/09188) by the present inventors is exemplified.

Figure 1:
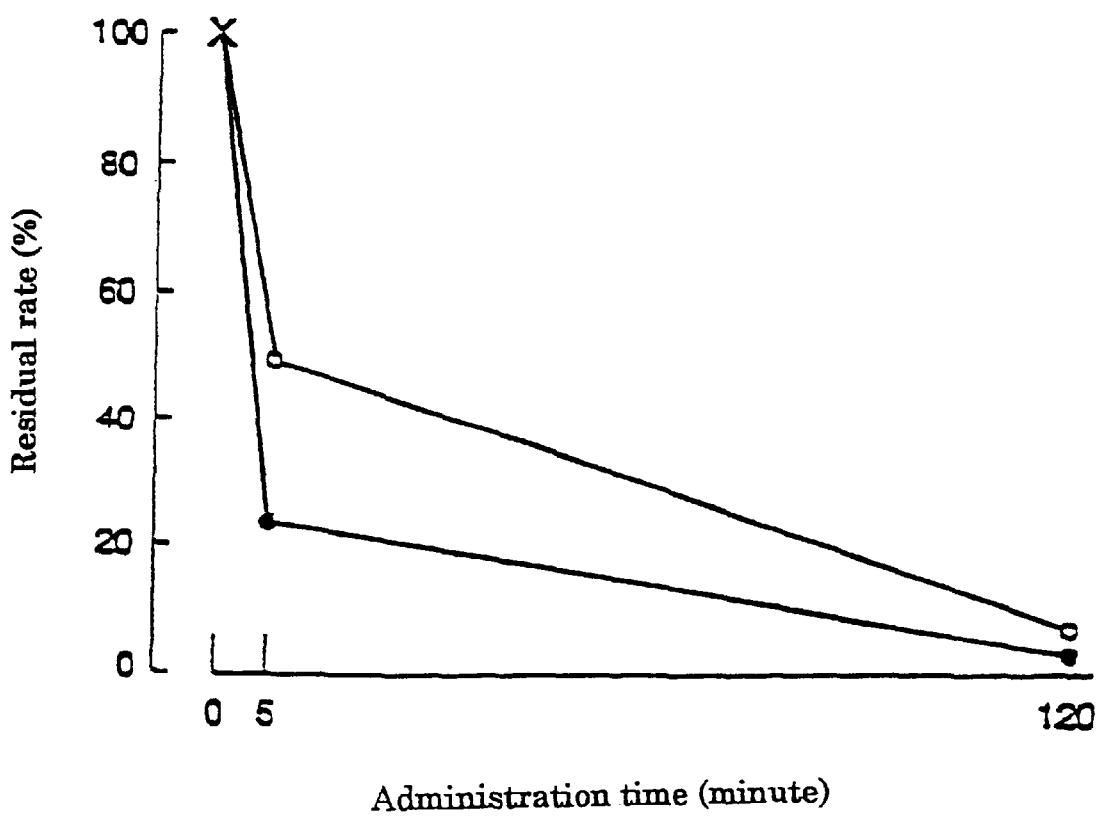
FIG. 1 exhibits the results of analysis of the concentration of dermatan sulfate in blood (residual rate) with the passage of time after administering deramatan sulfate with different origins in rat. In the figure, ○ exhibits dermatan sulfate derived from crest, and ● exhibits dermatan sulfate derived from bovine intestine. X represents overlapping ○ and ●.

Dermatan sulfate derived from crest and dermatan sulfate derived from bovine intestine (see reference example 2 in WO95/09188) were administered into tail vein of SD male rats and changes with the passage of time in the residual level of dermatan sulfate in blood were determined and the residual rate thereof to the initial level of dermatan sulfate on administration was calculated (see example 1 in the above International publication). Changes with the passage of time in residual rate of the two compounds in blood after administration were demonstrated in FIG. 1. ○ in the figure represents dermatan sulfate derived from crest and ● represents dermatan sulfate derived from bovine intestine. As the results shown in FIG. 1, the residual rate of dermatan sulfate derived from crest at 5 minutes after administration was twice as much as that of dermatan sulfate derived from bovine intestine and even at 120 minutes after administration dermatan sulfate derived from crest remained about 10% while dermatan sulfate derived from bovine intestine was scarcely detected. Thus, since dermatan sulfate derived from crest or dermatan sulfate with the equivalent physical properties has a long life span in blood and sustained anti-inflammatory effects, a large dosage thereof is not required for the treatment and dermatan sulfate derived from crest or equivalent thereof is the most preferable.

As an anti-inflammatory agent of the present invention, pharmaceutically acceptable salt of dermatan sulfate can be used. As such a salt, though it is not limited, sodium salt, potassium salt, lithium salt or calcium salt is preferable and sodium salt is usually administered.

Dermatan sulfate is usually administered intravenously but, if necessary, it can be administered intra-arterially, intramuscularly or percutaneously. Eyedrops thereof can be prepared in combination with an appropriate acceptable auxiliary ingredient and used for instillation. Ointment or cream thereof can be also prepared in combination with an appropriate base and coated on skin or mucosa. Further, oral drug can be also prepared by devising dosage form.

In order to prepare an anti-inflammatory agent an agent enhancing anti-inflammatory effect or a pharmaceutical of the present invention, effective amount of dermatan sulfate or glycosaminoglycan having sulfate group and/or immunosuppressing compound (immunosuppressant) can be appropriately used with auxiliary ingredients such as usual stabilizer, emulsifier, isotonic agent and/or pH conditioner which are acceptable for medicine.

Dose of dermatan sulfate or pharmaceutically acceptable salt thereof for an adult per day is 50–3,000 mg. Administration thereof can be carried out singly or divided into more than 2 times or can be continuous intravenous infusion for several days.

Further, glycosaminoglycan having sulfate group in combination with immunosuppressant can significantly enhance anti-inflammatory effect of immunosuppressant and decrease the amount of immunosuppressant. As a result, serious adverse effects of immunosuppressant due to immunosuppressant administration can be lightened. Accordingly, pharmaceutical drugs comprising glycosaminoglycan having sulfate group as an effective ingredient can enhance anti-inflammatory effect of immunosuppressant and used as an agent enhancing anti-inflammatory effect of immunosuppressant and reducing the dose thereof, an agent decreasing the adverse effects of immunosuppressant or an agent in combination with immunosuppressant which enhances anti-inflammatory effects and decreases adverse effects of said immunosuppressant. As glycosaminoglycan used having sulfate group used in combination with an immunosuppressant, dermatan sulfate, especially dermatan sulfate with the above physical properties and origin or pharmaceutically acceptable salt thereof is preferable.

As far as glycosaminoglycan having sulfate group and an immunosuppressant are administered in the same individual (patient), combined modality (timing of administration, administration route) is not restricted, wherein pharmaceutical comprising single effective component can be prepared independently and pharmaceutical comprising glycosaminoglycan having sulfate group can be administered before or after administration of an immunosuppressant or pharmaceutical composition comprising both components can be also prepared and administered. More specifically, glycosaminoglycan having sulfate group or pharmaceutically acceptable salt thereof can be prepared in the form for infusion and an immunosuppressant can be prepared in the form for oral administration or infusion.

The dose of an immunosuppressant in combination with glycosaminoglycan having sulfate group depends on types of immunosuppressant, patients conditions (age, sex, type of disease, seriousness, etc.), administration method (administration route, dosage form, etc.) and can not define generally, but 30–70% of dose of an immunosuppressant to the dose thereof on a single administration is generally preferable.

As an immunosuppressing compound or an immunosuppressant used in combination with an agent enhancing anti-inflammatory effect or glycosaminoglycan having sulfate group, any immunosuppressant having anti-inflammatory effect, any commercially available or known immunosuppressant can be used (see "Today's remedy (1994)", 1994, Nankodo publ; 157–161p "Immunosuppressants", and 162–183p, "Adrenocortical steroid"). As an immunosuppressant or an immunosuppressing compound, adrenocorticosteroid, cyclophosphamide, azathioprine, mizoribine, cyclosporine, methotrexate, tacrolimus hydrate, etc. can be exemplified. As typical adrenocorticosteroid, prednisolone, methyl prednisolone, betamethasone, dexamethasone, paramethasone, triamcinolone, hydrocortisone, and cortisone acetate can be exemplified.

The anti-inflammatory agent of the present invention exhibits an anti-inflammatory action against inflammation accompanied with the following diseases and can prevent, treat or relief these diseases of mammal including human (primates including human; pet animals such as dogs, cats, etc.; livestocks such as cattles, pigs, horses, etc.) and birds (chicken, etc.).

(1) Glomerulonephritis

According to the classification of WHO (Churg, J. & Sokin, L H: Renal disease classification and atlas of glomerular disease. Tokyo and New York, Igaku-shoin, 1982), glomerulonephritis is divided into 1) primary glomerular diseases, 2) glomerulonephritis of systemic diseases, 3) glomerular lesions in vascular diseases, 4) glomerular lesions in metabolic diseases, 5) hereditary nephropathies, 6) miscellaneous glomerular disease, 7) end stage kidney and 8) glomerular lesions following transplantation. An anti-inflammatory agent of the present invention is effective for primary glomerular diseases of the above item 1) (A. minor glomerular abnormalities, B. focal/segmental lesions, C. diffuse glomerulonephritis and D. unclassified glomerulonephritis) and specific diseases (lupus nephritis, anaphylactoid purpura, IgA nephropathy (Berger's Disease), Goodpasture's syndrome) in glomerulonephritis of systemic diseases of item 2). Further, it is effective for glomerular lesions in vascular diseases of item 3) (periarteritis nodosa, Wegener's granulomatosis, thrombotic microangiopathy, glomerular thrombosis, benign nephrosclerosis, malignant nephrosclerosis and scleroderma) and glomerular lesions following transplantation of item 8).

(2) Collagen Diseases and Related Diseases

Collagen diseases and related diseases correspond to diffuse connective tissue diseases classified by American Rheumatology Association (Decker, J. L. et al., Arthritis Rheum. 26, 1029, 1983).

Diseases belonging to the above category comprise rheumatoid arthritis, juvenile arthritis, lupus erythematosus, scleroderma, diffuse fasciitis, polymyositis, necrotizing vasculitis and other forms of vasculopathy (polyarteritis nodosa, allergic granulomatosis, hypersensitivity angiitis, granulomatous arteritis, Kawasaki disease, Behcet's disease, etc.), Sjogren's syndrome, Overlap syndromes, others (polymyalgia rheumatica, relapsing panniculitis, relapsing polychondritis, lymphomatoid granulomatosis, erythema nodosum, etc.). In addition, glomerulonephritis and vasculitis caused by these diseases are also included. The anti-inflammatory agents of the present invention are effective for these diseases. Further, they are also effective for human autoimmune lymphoproliferative syndrome (Cell 81, 935–946(1995), Science 268, 1347–1349(1995)).

(3) Intractable Vasculitis

According to Fauci, AS (The vasculitis syndrome. Harrison's Principles of Internal Medicine, 11th ed., McGraw-Hill Book Company, 1986), intractable vasculitis is classified into systemic necrotizing vasculitis (classical multiple arteritis, allergic granulomatous angiitis (Churg-Strauss syndrome), polyarteritis nodosa complicated syndrome), hypersensitivity vasculitis (exogenous stimuli proven or suspected; Schoenlein-Henoch purpura, serum sickness and sickness-like reactions, other drug-induced vasculitis, vasculitis associated with infectious diseases, endogenous antigens likely involved; vasculitis associated with neoplasms, vasculitis associated with connective-tissue diseases, vasculitis associated with other underlying diseases, vasculitis associated with congenital deficiencies of the complement system), Wegener's granulomatosis, giant cell arteritis (temporal arteritis, Takayasu's arteritis), other vasculitis syndromes (Kawasaki disease, isolated central nervous system vasculitis, Buerger's disease (thromboangiitis obliterans) and the anti-inflammatory agents of the present invention are effective for these diseases.

(4) Immunogical Anomalies or Autoimmune Diseases

As immunogical anomalies or autoimmune diseases, inflammation accompanied with rejection after transplantation of various organs comprise; nerve diseases include multiple sclerosis, Guillan-Barre syndrome, HTLV-1 associated myelopathy and the like; gastrointestinal diseases include inflammatory intestinal diseases (clone disease, ulcerative colitis), primary biliary cirrhosis and the like; endocrinological diseases include autoimmune thyroid gland diseases such as Hashimoto disease, Basedow disease, insulin-dependent diabetes mellitus (insulitis,) and the like; diseases in circulation system include idiopathic myocarditis, Chagas myocardosis, dilated cardiomyopathy, endocardial myofibrosis cordis, idiopathic benign pericarditis, eosinophilic endocarditis, postcardiotomy syndrome, postmyocardial infarction syndrome, antiphospholipid-antibody syndrome and the like; respiratory diseases include idiopathic interstitial pneumonia, lung fibrosis and the like; renal diseases include interstitial nephritis and the like; dermal diseases include pemphigus, pemphigoid, immunogenic hydrosa acquired epidermolysis bullosa and the like; ophthalmic diseases include lens-induced uveitis, Vogt-Koyanagi-Harada syndrome and the like (Autoimmune diseases and immunodeficiency, Recent internal medicine 22, Imura Hiroo, ed. Nakayama-shoten, 1993, pp9–206). The anti-inflammatory agents of the present invention are effective for these diseases.

The present invention will be described by exemplifying reference examples, examples, comparative examples as follows:

Reference Example 1
Preparation of Dermatan Sulfate

One kilogram of crest (from hen) was minced and boiled. To the residue, 5 g of pronase (Kaken-seiyaku, trade name) was added, which was kept to digest it at 50° C. for 12 hours. The digested solution was filtered through diatomaceous earth and pH of the filtrate was adjusted to 5.8–6.3. Hyaluronidase (1,000 TRU) derived from streptomyces griceus (Seikagaku-Corporation) was added thereof, which was kept to digest it at 50° C. for 3 hours. Sodium chloride was added to the solution so as to be 0.65 M, which was applied on an anion exchange resin Diaion HPA-10 (Mitsubishi-chemical, trade name) column (3×20 cm) equilibrated with 0.5 M saline solution. After the column was washed with 0.5 L of 0.65 M saline solution and, consecutively, with 0.3 L of 1.1 M saline solution, fractions eluted with 1.8 M saline solution were collected and concentrated under reduced pressure. The concentrate was dialyzed against distilled water over night and concentrated to 10 ml, to which 5 M sodium hydroxide solution was added so that the final concentration thereof would be 0.5 M. After this alkaline solution was kept at 37° C. for 90 minutes, it was cooled and neutralized with acetic acid. After the addition of ethanol of twice amount to the neutralized solution, resulting precipitate was washed with 70% ethanol, pure ethanol and ether consecutively and dried under reduced pressure in the presence of phosphorus (V) oxide. After dried material (5 g) was left in 125 ml water over night, a small amount of insoluble substance was removed by centrifugation (10° C., 10,000 rpm for 15 minutes), to which 125 ml sodium acetate aqueous solution was added and ethanol was also added so that the final concentration thereof would be 45% in an ice bath. It was kept at 4° C. for 20 hours and centrifuged to give precipitate, which was washed with 90% ethanol, pure ethanol and ether consecutively and dried under reduced pressure in the presence of phosphorus (V) oxide to yield purified sodium salt of dermatan sulfate (hereinafter, may be abbreviated as DS).

The average molecular weight, intrinsic viscosity and disaccharide composition thereof were demonstrated in Table 1. Of course, the method of isolation and purification of DS is not limited as the above and the method described in published examined Japanese patent application 9042/1985 or published examined Japanese patent application 21241/1986 may be used.

(1) Determination of Average Molecular Weight

The average molecular weight of DS was determined according to the method of Arai et al. (Biocim. Biophys. Acta, 1117, 60–70, 1992). Using glycosaminoglycan with known molecular weight determined by light scattering method as standard, it was determined by eluting position of gel permeation using high performance liquid chromatography (HPLC), wherein three columns, that is, TSK gel G4000PWX$_L$, TSK gel G3000PWX$_L$ and TSK gel G2500PWX$_L$ (anyone 300×7.8 mm in the inside diameter, Toso) which were connected with the next one, were used.

As eluting solvent, 0.2 M saline solution was used at the flow rate of 0.6 ml/min. and detection was carried out by differential refractometry.

(2) Disaccharide Analysis

According to a known method (see "2·8 Structural analysis by HPLC using glycosaminoglycan degrading enzyme" described in Shin-seikagaku-jikken-kouza 3, Tousitu II, p49–62, (1991, Tokyo-kagaku-dojin)), analysis of site of sulfate group in DS was carried out as described below. DS was digested with chondroitinase ABC and the resulting disaccharide (unsaturated disaccharide) fraction including unsaturated disaccharide was analyzed by high performance liquid chromatography (HPLC), whose result was compared with the HPLC analytical result of the product obtained by treating said unsaturated disaccharide fraction with chondro-6-sulfatase. Experimental conditions of digestion with chondroitinase ABC and desulfurization with chondro-6-sulfatase and HPLC analysis were described as follows:

a) Digestion with Chondritinase ABC

According to a method of Yoshida et al. (Anal. Biochem., 77, 372–333(1989)), 20 μl of 0.4 M tris-HCl (pH 8.0), 20 μl of 0.4 M sodium acetate, 20 μl of 0.1% bovine serum albumin and 120 μl of water were added to 20 μl of DS aqueous solution (10 mg/ml) and 20 μl of chondroitinase ABC (5 U/ml) was added thereto, which was kept at 37° C. for 2 hours.

b) Digestion with Chondro-6-sulfatase

To 100 ml of the above chondroitinase ABC-digested product, 20 μl of chondro-6-sulfatase (5 U/ml) dissolved in 20 mM tris-acetate buffer solution (pH 7.0) was added, which was kept at 37° C. for 2 hours.

C) Analysis by HPLC

50 μl of the above solution of chondroitinase ABC-digested product or the solution of chondro-6-sulfatase-digested product was analyzed by HPLC (Hitachi Seisakusho), wherein ion exchange column (YMC-Pack PA-120-S5 column, 250×2.6 mm in the inside diameter) was used and absorbance at 232 nm was determined. Elution was carried out by gradient 0–100% of 800 mM sodium hydrogenphosphate for 60 min. at the flow rate of 1.5 ml/min. Eluted peaks of unsaturated disaccharides having sulfate group at different site were identified.

(3) Measurement of Intrinsic Viscosity

According to 12th ed. Japanese Pharmacopeia, intrinsic viscosity of DS was measured.

Analytical instrument: Automatic viscosity measuring instrument, VMC-052 (Rigo) using Ubbelohde viscometer.

Solvent: 0.2 M sodium chloride solution (the same solution was used for measuring flowing down time through a viscometer).

Measuring temperature: 30±0.1° C.

Measuring method: Intrinsic viscosity was determined from the vertical axis intercepts wherein reducing viscosity (η red) was plotted on a vertical axis and sample's concentration was plotted on a horizontal axis.

$$\eta\text{red}=(t_s/t_0-1)/C$$

in the above equation, $t_s$: flowing rate of 0.2 M sodium chloride solution containing DS, $t_0$: flowing rate of solvent (0.2 M sodium chloride solution containing no DS), C: sample's concentration (weight %).

In Table 1, the measuring results of physical properties of the above DS derived from crest and other known DS (bovine intestine, porcine intestine, porcine skin) were summarized. DS derived from bovine intestine, porcine intestine and porcine skin were prepared according to the method described in Patent application WO95/09188.

EXAMPLE 1

Effects of DS and low molecular weight heparin (LMWHep; trade name, Fragmin, Pharmacia, Kissei-yakuhin-kogyo) on blood clotting were investigated.

(1) Experimental Material

Ten weeks old male C57BL/6 mice (one group consisted of 3 mice) were used. DS and LNWHep were dissolved in sterile physiological saline solution.

(2) Experimental Method

After DS (25 mg/kg) and LNWHep (1 mg/kg) were administered into mice tail vein, blood samples were taken with the passage of time and active partial thromboplastin time (APTT) thereof was measured.

(3) Results

Figure 2:
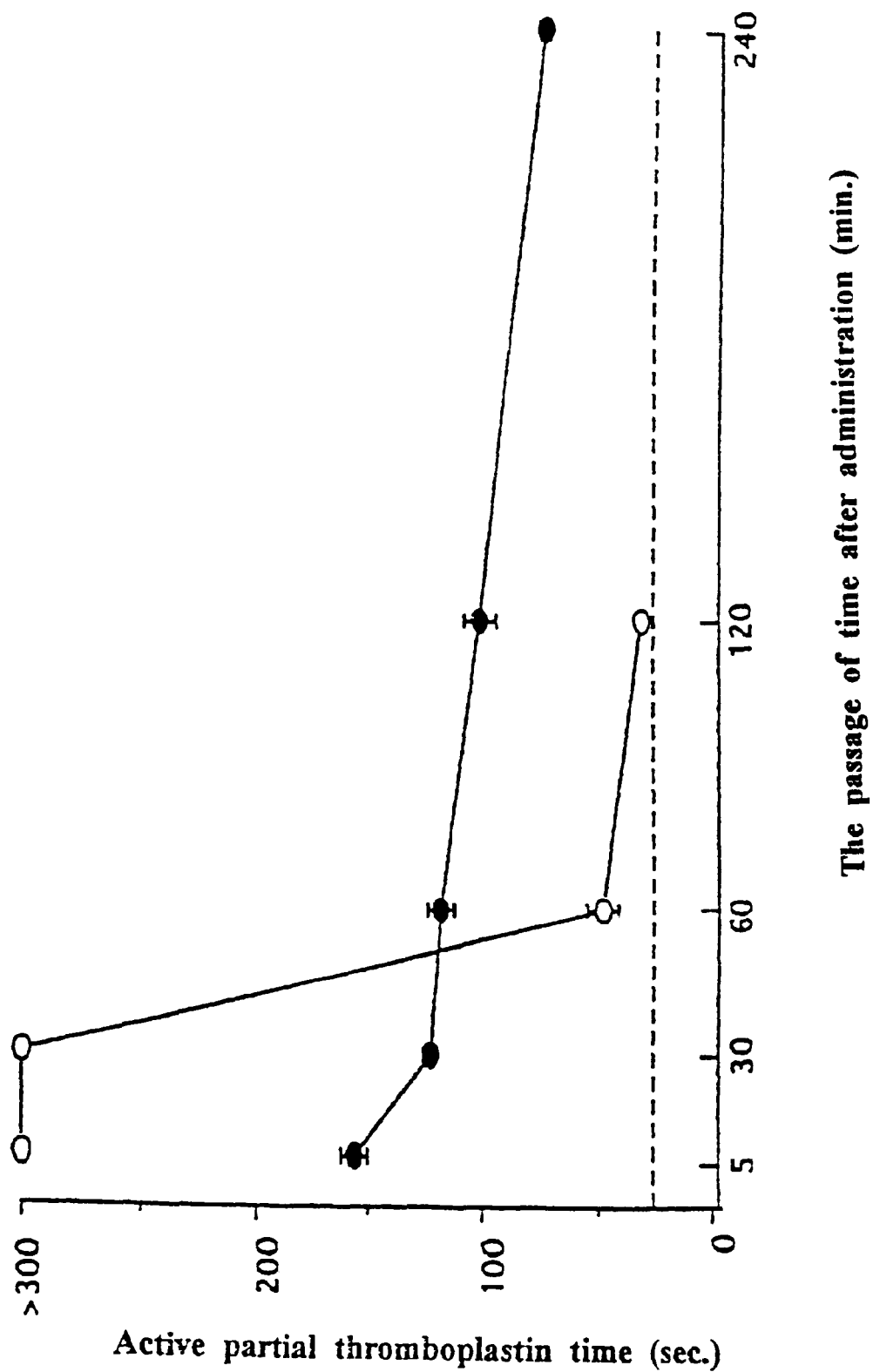
FIG. 2 exhibits the effects of dermatan sulfate on blood clotting in mice in example 1. In the figure, ○ represents administration of low molecular weight heparin and ● represents administration of dermatan sulfate.

Changes with the passage of time with respect to APTT after administration of each agent were demonstrated in FIG. 2, wherein ○ represents the case of LMWHep administration and ● represents the case of DS administration (means±standard errors (sec)). As in FIG. 2, APTT in LMWHep (○) was still over 300 seconds even at 30 minutes after administration, which means that LMWHep suppressed an action of blood clotting factor and augmented risk of hemorrhage very much. In contrast, over 60 minutes after administration, APTT prolonging activity was not recognized, which means that LMWHep was removed from blood for a short time and sustained effects thereof for long duration could not be expected. On the other hand, at 5 minutes after administration of DS, only mild APTT prolonging activity of DS (●)was observed, which means no risk of hemorrhage. Further, such activity was recognized even at 240 minutes after administration, which suggested that DS had safer and more sustained effects than LMWHep. As described above, because over 1 mg/kg of LMWHep may cause adverse effect of hemorrhage, maximum dose of LMWHep was 1 mg/kg in the following experiments. Because even LMWHep which was improved with respect to anti-coagulant activity might cause hemorrhage as described before, treatment with heparin (Hep) was not expected to be practical and, accordingly, was not carried out.

EXAMPLE 2

Study Using Mice SLE Model-I
Confirmation of the Effects of Single Use of Dermatan Sulfate (1) Experimental Material As SLE model, 17 weeks old male MRL (1 pr/1 pr) mice were used, while C57BL/6 mice with the same age and sex were used as normal control. As agents, DS or low molecular weight heparin (LMWHep, Fragmin) prepared according to a method in reference example 1 was dissolved in sterile physiological saline solution on use.

(2) Experimental Method

Blood samples were taken from 17 weeks old mice, only MRL mice with nephritis whose level of blood urea nitrogen (BUN) were high at the nearly same level were selected and divided into 4 groups, each group consisting of 5 mice. Sterile physiological saline solution was administered in one group as non-treated control group, 5 mg/kg of DS, 25 mg/kg of DS and 1 mg/kg of LMWHep were administered into tail vein in another 3 groups, once per day and five times per week. After 4 weeks, blood samples were taken under anesthesia with Nembutal and kidneys were excised after animals were killed by exsanguination. Serum and plasma taken were used for determination of BUN, creatinine and fibrinogen and kidneys were used for histopathological examination.

(3) Results (See FIGS. 3–6)

1) Effects on Renal Function

Figure 3A:
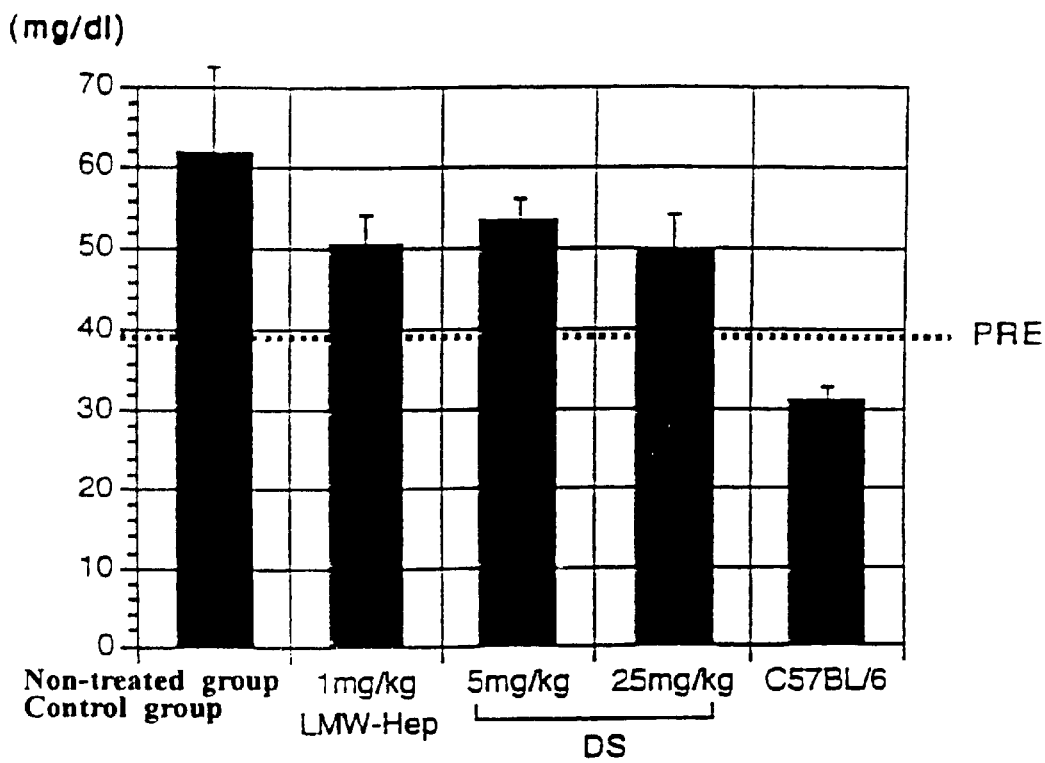
FIG. 3 exhibits the effects of dermatan sulfate on serum level of serum component reflecting renal function in mice in example 2.
Figure 3B:
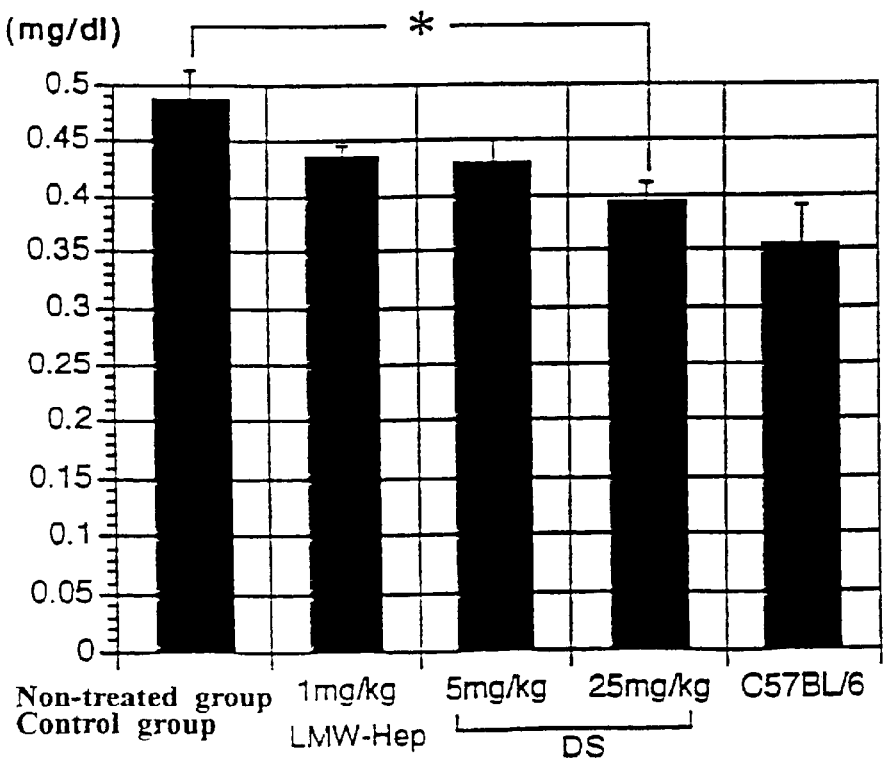

Analytical results of BUN and creatinine were demonstrated in FIG. 3a and in FIG. 3b, respectively (serum level (mg/dL) of each substance depicted in the figures). In FIG. 3a, PRE (dotted line) exhibits mean BUN at the initiation of administration of agents (17 weeks old). As shown in the figure, that value was clearly higher than that of normal control group (C57BL/6), which exhibited that MRL mice developed nephritis. In FIG. 3b, * means that there is a significant difference with $p<0.05$ from non-treated control group by Bonferroni examination. Both of BUN and creatinine level of non-treated control group were higher than those of normal control group(C57BL/6), which made it clear that renal function thereof was impaired. Among treated groups, BUN level was slightly improved in 5 mg/kg DS group, 25 mg/kg DS group and 1 mg/kg LMWHep group. Among treated group, creatinine level was also slightly improved in 5 mg/kg DS group and 1mg/kg LMWHep group and significantly improve in 25 mg/kg DS group.

2) Effects on Histopathological Observations of Kidney

FIGS. 4a–c demonstrates kidney histological figures, that is, histopathological changes of kidney at each step, on autopsy of MRL mice and normal control mice. FIG. 4a demonstrated histological figure of normal control and others, those of MRL mice (photomagnification:×500). The horizontal bar on the right bottom of each photograph exhibits 10 μm.

Figure 5A:
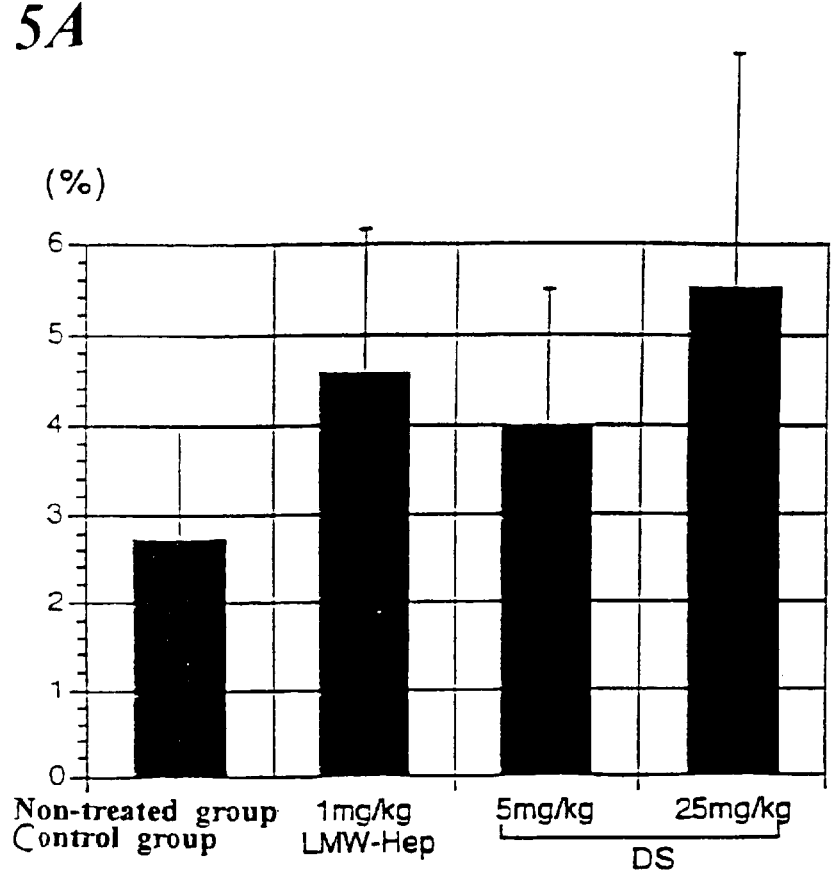
Figure 5B:
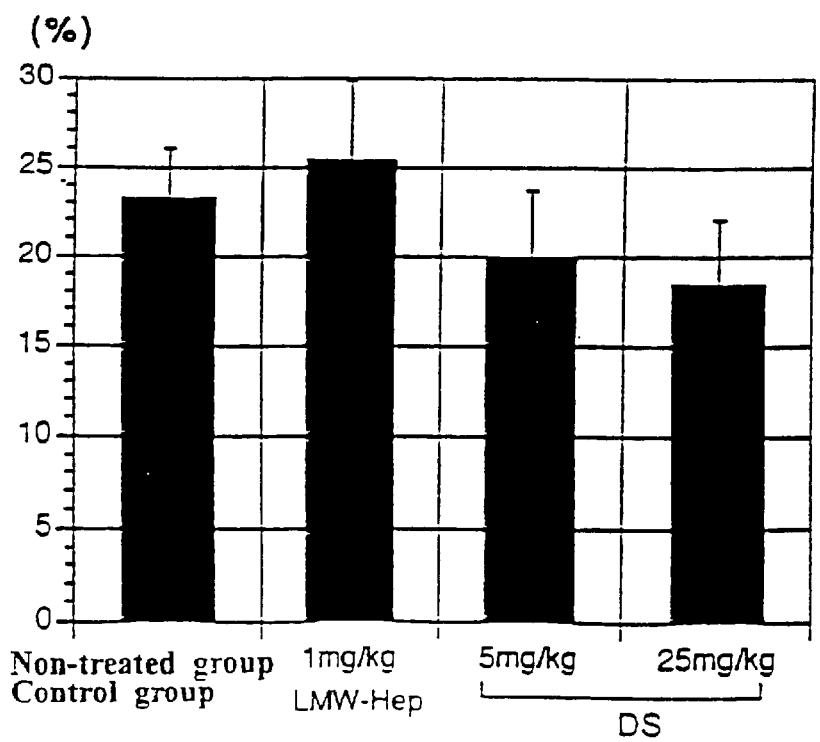

FIG. 5a exhibits the number of MC glomeruli/the total number of glomeruli (%) and FIG. 5b exhibits the number of DP glomeruli/the total number of glomeruli (%).

As a result of microscopic examination of autopsied mice kidney, clear figure of glomerulo nephritis was observed in non-treated control group, wherein normal glomeruli (FIG. 4a) was not observed, (1) minimal change (MC) type with slightly hypertrophic ansa and cell proliferation which is presumed to be classified by WHO (FIG. 4b), (2) glomeruli which almost completely lost Bowman's capsule cavity and vascular cavity and was filled with cellular components and precipitate, whose function was presumed to be lost (one corresponding to Proliferative Glomerulonephritis (hereinafter, abbreviated as DP) of Diffuse glomerulonephritis in WHO classification, FIG. 4c), and (3) one between the above (1) and (2). From these results, lesion of renal glomeruli of MRL (1 pr/1 pr) mice was thought to change gradually from MC to DP wherein Bowman's capsule cavity and vascular cavity lost due to proliferation of monocyte and mesangial cell and/or precipitation of fibrin and immune complex.

Measurement of the number of MC glomeruli/the total number of glomeruli (%) and the number of DP glomeruli/the total number of glomeruli (%) exhibited that the ratio of MC glomeruli significantly increased in 25 mg/kg DS group and slightly increased in 5 mg/kg DS group and 1 mg/kg LMWHep group (FIG. 5a). On the other hand, the ratio of DP glomeruli clearly decreased in a dose-dependent manner in 5 mg/kg DS group and 25 mg/kg DS group, while, in LMWHep group, such an effect was not recognized (FIG. 5b).

As described above, DS was found to have an effect of preventing the progress of nephritis by histopathological examination. LMWHep had a slight action of maintaining minimal change (MC) group but did not exhibit effect on already-progressed nephritis.

3) Effects on Histopathological Change of Renal Artery

Figure 6A:
Figure 6B:
Figure 6C:
Figure 6D:

FIG. 6a exhibits histological figure of renal artery of normal control mice and FIG. 6b–d exhibit histological figures of MRL mice renal artery, that is, histopathological changes of renal artery at each stage (photomagnification:× 204). The horizontal bar on the right bottom of each photograph shows 50 μm. As the results of microscopic examination, the following histopathological figures of 3 stages of angiitis in MRL mice renal artery were recognized:

slight degree: inflammatory cellular infiltration around blood vessel(FIG. 6b) intermediate degree: inflammatory cellular infiltration around blood vessel and collapse of tunica externa and tunica media (vacuolar degeneration, fibrin precipitation) (FIG. 6c)

serious degree: inflammatory cellular infiltration around blood vessel and collapse of tunica externa and tunica media (vacuolar degeneration, fibrin precipitation, proliferation of smooth muscle cell) and inflammatory infiltration in tunica interna and tunica media (FIG. 6d).

Angiitis in each group was histopathologically evaluated using these histological figures as parameter. As the results, in 25 mg/kg DS group, individual with serious degree decreased and individual with intermediate and slight degree increased (table 3). There was not a big difference among 1 mg/kg LMWHep group, 5 mg/kg DS group and non-treated group (table 3). From these histopathological observations, DS was found to have a suppressive effect on angiitis.

TABLE 3

|  | slight degree | intermediate degree | serious degree |
|---|---|---|---|
| Non-treated group | 0 | 2 | 3 |
| LMWHep 1 mg/kg group | 0 | 1 | 4 |
| DS 5 mg/kg | 0 | 2 | 3 |
| DS 25 mg/kg | 1 | 3 | 1 | number: the number of individual

4) Effects on Fibrinogen Level in Blood

Fibrinogen is one of the acute reactive substances and its level rises not only in glomerulonephritis and angiitis, but also in various kinds of inflammation and is considered to be one of the parameters of inflammation (In Procoagulant Activity in Health and Disease, Eds. Levy, G. A. and Cole, E. H. CRC Press Boca Raton 1994). As shown in FIG. 7, this variable parameter of MRL (1 pr/1 pr) mice non-treated group was significantly higher than that of normal control group, suggesting serious inflammation in the non-treated group. In 5 mg/kg and 25 mg/kg DS groups, this increase was suppressed in a dose-dependent manner but such an action did not scarcely recognized in LMWHer.

EXAMPLE 3

Study Using Mice SLE Model-2

Confirmation of Combined Effects of Dermatan Sulfate with Cyclophosphamide (1) Experimental Material Ten weeks old male MRL (1 pr/1 pr) mice was used as experimental animals and DS prepared according to reference example 1 was used as an agent by dissolving it in sterile physiological saline solution on use.

Endoxan for injection (Cyclophosphamide, Shionogi) was dissolved in each vial (100 mg/vial) by adding 5 ml of distilled water for injection and, further, sterile physiological saline solution was added thereto so that the concentration thereof would be 4, 6 and 8 mg/ml. Sterile physiological saline solution was administered in negative control group (non-treated group).

(2) Experimental Method

At the age of 10 weeks old, body weight of animals were weighed and blood samples were taken for determination of serum BUN (urea nitrogen) and serum creatinine. The animals were divided into 5 groups, each group consisting of 6 mice, by stratified continuous randomization so that the mean value and standard deviation in each group would have nearly the same as those in other group. DS was daily, 5 times per week (neither on Saturday or on Sunday), administered into tail vein in mice using 1 ml disposable syringe at the dose level of 25 mg/kg/day. Cyclophosphamide was intraperitoneal administered once a week at any dose of 20 mg/kg, 15 mg/kg or 10 mg/kg according to the method described in the reference where the same agent was studied in mice (Shiraki, M. et al., Clin. Exp. Immunol., 55, 333–339(1984)). During administration, animals were daily observed carefully. After 8 weeks, blood samples were taken under anesthesia with Nembutal and animals were killed by exsanguination. Then, serum creatinine level, spleen weight and the weight of mesenteric lymph node were measured.

(3) Results (see FIGS. 8–10)

1) Effects on Renal Function

In FIG. 8, analytical results of serum creatinine level (mg/dL) were shown. Comparing with the negative control group, single administration of 20 mg/kg of endoxan did not exhibit any effect on creatinine level at all. However, combined administration of endoxan (10 mg/kg and 20 mg/kg) with 25 mg/kg of DS resulted in a slight improvement with respect to creatinine level and combined administration of 15 mg/kg of endoxan with DS improved the level significantly ($p<0.05$). What should be attended especially was that both of the cases of combined administration of 20 mg/kg of endoxan with 25 mg/kg of DS and 15 mg/kg of endoxan with 25 mg/kg of DS gave better results than that of single administration of 20 mg/kg of endoxan. Further, the group of combined administration of 15 mg/kg of endoxan with 25 mg/kg of DS gave much better results than single administration group of 20 mg/kg of endoxan and, therefore, DS was found to suppress toxicity of endoxan and be effective.

2) Effects on Spleen Weight

Spleen weight in MRL mice is abnormally heavier than that in normal mice. Treatment for enlarged spleen in MRL mice was tried. In FIG. 9, measuring results of spleen weight were shown. Comparing with negative control group, single administration group of 10 mg/kg of endoxan did not give any effect but all the other groups gave effective results on splenomegaly. The dose of DS was 25 mg/kg in any case. As noteworthy results, if the same amount of endoxan was used, combined modality group of endoxan with DS gave better results than single administration group of endoxan.

3) Effects on the Weight of Mesenteric Lymph Node

The weight of mesenteric lymph node in MRL mice is abnormally heavier than that in normal mice. Treatment for this anomaly was tried. Weighing results of mesenteric lymph node were shown in FIG. 10. Comparing with the negative control group, decreases in the weight of lymph node was observed in the all other groups. It was important that combined modality group of 10 mg/kg of endoxan with DS gave better results than the single administration group of 10 mg/kg of endoxan. The dose of DS was 25 mg/kg in any case.

From the results of example 3, combination of DS with an immunosuppressant was found to enhance anti-inflammatory effect of an immunosuppressant and give same or better effect than a single application of an immunosuppressant at a certain dose level (hereinafter, referred to dose A). That is, combination of less than dose A of an immunosuppressant with DS (The dose of DS is not limited.) was found to give better effect than a single dose A of immunosuppressant. Because DS is one of glycosaminoglycans having sulfate group, combination of other glycosaminoglycan having sulfate group with an immunosuppressant will give such an effect.

EXAMPLE 4

Study Using Rat Multiple Sclerosis (MS) Model

The effects of DS on rat experimental allergic encephalomyelitis (EAE) as an animal model of multiple sclerosis which is a typical disease of immunological anomaly in central nervous system and thought to be related to autoimmune (Clinical immunology illustrated, p 112–117, Brostoff, Scadding, Male, Roitt ed., Shun-ichi Hirose, Shogo Kano, Tomio Tada, transl., Nanko-do, 1994) were studied.

(1) Experimental Materials

As experimental animals, 4 weeks old female Lewis rats were used and divided into 2 groups, each group consisting of 10–11 rats. As immunizing substance, myelin basic protein of guinea pig (hereinafter, referred to GPMBP) was used with Freund's complete adjuvant including Mycobacterium tuberculosis (MTB). As agents, DS prepared according to the method of reference example 1 was used by dissolving in sterile physiological saline solution on use. Hereinafter, referred the group administered with DS to DS group. In the negative control group, sterile physiological saline solution was administered.

(2) Experimental Methods

Each rat was immunized at its foot with injection of 12.5 μg of GPMBP and 200 μg of MTB. Since the third day after immunization, 5 mg of DS and sterile physiological saline solution were intraperitoneally administered once a day in DS group and in the negative control group, respectively. Clinical symptoms characteristic to EAE were defined numerically as the following: (hereinafter, referred toclinical score) nosymptom, 0; tail hypotonia, 1; inferior limb hypotonia, 2; inferior limb paralysis, 3; superior limb paralysis, 4; death, 5.

Symptoms of each rat were daily expressed numerically and the onset day of disease and accumulated clinical scores were studied in each group. Significant difference was examined by Student t-test.

(3) Results

With respect to accumulated clinical scores, there was a significant difference (p<0.05) between DS group (12.4±1.7) and control group (16.3±5.9), suggesting that DS suppressed symptoms. In addition, mean onset day in DS group was 9.5±0.5 and that in control group was 9.1±0.3, suggesting that expression of symptoms was inclined to prolong in DS group and that DS suppressed expression of symptoms. From these results, DS was found to be an effective agent for treatment of MS, because EAE is an animal model of MS.

EXAMPLE 5

Toxicity test by single intravenous administration of dermatan sulfate(1) Experimental method As experimental animals, five weeks old female and male Cri; CD-1 mice (Japanese Charles-river (n=5 each) were used. The DS solution obtained by the same method as in reference example 1 was made isotonic using sterile distilled water and sterile physiological saline solution and single 2000 mg/kg of DS was administered intravenously into tail vein in mice and clinical observations were carried out for 14 days.

(2) Results

After 14 days observation, there was no death among both 5 female and 5 male mice. Accordingly, the fetal dose of DS under the above conditions was estimated more than 2000 mg/kg.

EXAMPLE 6

Pharmaceutical (1) Injections comprising dermatan sulfate as an effective ingredient DS (5000 mg) was dissolved in 100 ml of physiological saline solution, sterilized and injected into an ampoule (5 ml each), which can be used for intravascular injection, subcutaneous injection or intramuscular injection.

(2) Combined Use with Immunosuppressant

Various kinds of immunosuppressant with the dose described below were dissolved in 100 ml of physiological saline solution, sterilized and injected into ampoules. Depending on the kind of immunosuppressant, the dose thereof was determined, that is, cyclophosphamide, 30 mg; azathioprine, 30 mg; mizoribine, 150 mg; methotrexate, 3 mg; tacrolimus hydrate, 3 mg; cyclosporine 15 mg.

These immunosuppressants were combined with DS injections obtained in the above 1.

Before or after the administration of the above immunosuppressants, DS preparations can be administered. For example, 25 mg/day of prednisolone, 30 mg/day of cyclophosphamide or azathioprine, 150 mg/day of mizoribine, 3 mg/day of methotrexate or tacrolimus hydrate or 15 mg/day of cyclosporine can be used.

The effects of these immunosuppressants on various diseases can be enhanced by DS preparations administered before or after then. In addition, these dose can be varied depending on seriousness of patients. Among these agents, prednisolone, cyclophosphamide, methotrexate and cyclosporine can be administered intravascularly or orally. The primary administration route of other agents is per os.

Industrial Utility

Dermatan sulfate or pharmaceutically acceptable salt thereof can be used as a useful anti-inflammatory agent without adverse effects suppressing intractable, or protracted inflammation or inflammation in which immunological mechanism participates.

Further, when glycosaminoglycan having sulfate group or pharmaceutically acceptable salt thereof is used in combination with an immunosuppressant such as adrenocortical steroid, cyclophosphamide, azathioprine, mizoribine, cyclosporine, methotrexate, tacrolimus hydrate etc., smaller amount of immunosuppressant than in the case of single administration of an immunosuppressant can exhibit the same effect, resulting in decrease in the adverse effects induced by immunosuppressant.

What is claimed:

1. A method of treating inflammation in a mammal in need thereof, which comprises administering an effective amount of an anti-inflammatory composition comprising dermatan sulfate or a pharmaceutically acceptable salt thereof as an effective ingredient, and a suitable carrier to said mammal, wherein said dermatan sulfate comprises a content of unsaturated disaccharide having the formula (I):

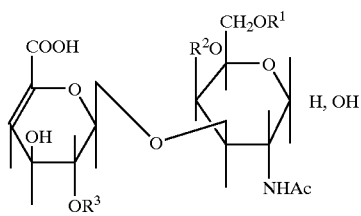

(I)

wherein $R^1$, $R^2$, and $R^3$ are each a hydrogen atom, of from 2 to 9% determined by degradation by enzyme to unsaturated dissacharide and high performance liquid chromatography, and wherein said dermatan sulfate has an average molecular weight determined by gel permeation chromatography using a glycosaminoglycan of a known molecular weight as a standard and high performance liquid chromatography of from 25,000 to 100,000 Daltons.

2. The method of claim 1, wherein said inflammation is caused by a protracted inflammatory disease or an inflammatory disease involving an immunological mechanism.

3. The method of claim 1, wherein said anti-inflammatory composition exhibits an anti-inflammatory action against an autoimmune disease.

4. The method of claim 1, wherein said anti-inflammatory composition exhibits an anti-inflammatory action against multiple sclerosis.

5. The method of claim 1, wherein said anti-inflammatory composition exhibits an anti-inflammatory action against collagen disease.

6. The method of claim 1, wherein said anti-inflammatory composition exhibits an anti-inflammatory action against glomerulonephritis.

7. The method of claim 1, wherein said anti-inflammatory composition exhibits an anti-inflammatory action against intractable vasculitis.

8. The method of claim 1, wherein said dermatan sulfate has an intrinsic viscosity (100 ml/g) measured at 30±0.1° C. using an Ubbelohde viscometer and 0.2 M sodium chloride solution as a solvent of from 0.8 to 2.0.

9. The method of claim 1, wherein said dermatan sulfate comprises a content of said unsaturated disaccharide of 3 to 8%.

10. The method of claim 1, wherein the dermatan sulfate is obtained from crest.

* * * * *